(12) United States Patent
Knutson et al.

(10) Patent No.: US 8,759,792 B2
(45) Date of Patent: Jun. 24, 2014

(54) NON-CONTACT TOTAL EMISSION DETECTION METHOD AND SYSTEM FOR MULTI-PHOTON MICROSCOPY

(75) Inventors: Jay R. Knutson, Kensington, MD (US); Christian A. Combs, Olney, MD (US); Robert S. Balaban, Bethesda, MD (US)

(73) Assignee: The United States of America, as Represented by the Secretary, Dept. of Health and Human Services, Washington, DC (US)

( * ) Notice: Subject to any disclaimer, the term of this patent is extended or adjusted under 35 U.S.C. 154(b) by 158 days.

(21) Appl. No.: 13/383,248

(22) PCT Filed: Jul. 12, 2010

(86) PCT No.: PCT/US2010/041723
§ 371 (c)(1),
(2), (4) Date: Aug. 6, 2012

(87) PCT Pub. No.: WO2011/006162
PCT Pub. Date: Jan. 13, 2011

(65) Prior Publication Data
US 2013/0153788 A1    Jun. 20, 2013

Related U.S. Application Data

(60) Provisional application No. 61/224,772, filed on Jul. 10, 2009.

(51) Int. Cl.
*H01J 65/08* (2006.01)
(52) U.S. Cl.
USPC ................................................. 250/459.1

(58) Field of Classification Search
USPC ................................................. 250/459.1
See application file for complete search history.

(56) References Cited

U.S. PATENT DOCUMENTS 5,034,613 A * 7/1991 Denk et al. ............... 250/458.1
5,088,823 A * 2/1992 Smith et al. .................. 356/328
(Continued)

FOREIGN PATENT DOCUMENTS

WO     2007/041458 A2    4/2007

OTHER PUBLICATIONS

Authors: Christian A. Combs*, Aleksandr V. Smirnov†, Jason, D. Riley‡, Amir H. Gandjbakhche‡, Jay R. KNUTSON† & Robert S. Balaban, Title: Optimization of multiphoton excitation microscopy by total emission detection using a parabolic light reflector, Data: Jun. 21, 2007, Publisher: Journal of Microscopy, vol. 228, Pt 3 2007, pp. 330-337.*
Author: Winfried Denk, Publisher: Wikipedia, Date: 1990.*

*Primary Examiner* — David Porta
*Assistant Examiner* — Taeho Jo
(74) *Attorney, Agent, or Firm* — Polsinelli PC; Teddy C. Scott, Jr.; Ron Galant

(57) ABSTRACT

A multi-photon microscope having an illumination source that transmits an illumination light into a housing having an objective lens arrangement for illuminating a sample disposed outside the housing and directing a first portion of emission light emitted from the sample to a detection system is disclosed. A light collection system is disposed proximate the objective lens arrangement for directing a second portion of emission light in a coaxial relationship with the first portion of emission light to the detection system such that substantially all of the emission light on, around and above the illumination region is detected.

19 Claims, 6 Drawing Sheets

(56) References Cited

U.S. PATENT DOCUMENTS

| | | |
|---|---|---|
| 6,373,070 B1 | 4/2002 | Rasmussen |
| 6,667,830 B1 | 12/2003 | Iketaki |
| 2007/0057211 A1* | 3/2007 | Bahlman et al. ............. 250/584 |
| 2007/0115468 A1* | 5/2007 | Barnard ........................ 356/300 |
| 2008/0063345 A1* | 3/2008 | Balaban et al. ............... 385/115 |
| 2008/0130093 A1* | 6/2008 | Silberberg et al. ............ 359/298 |
| 2008/0315119 A1* | 12/2008 | Blackmore et al. ......... 250/459.1 |
| 2009/0091566 A1* | 4/2009 | Turney et al. ................. 345/419 |
| 2011/0044910 A1* | 2/2011 | Lin et al. ....................... 424/9.6 |
| 2011/0170180 A1* | 7/2011 | Turner et al. ................. 359/385 |

* cited by examiner

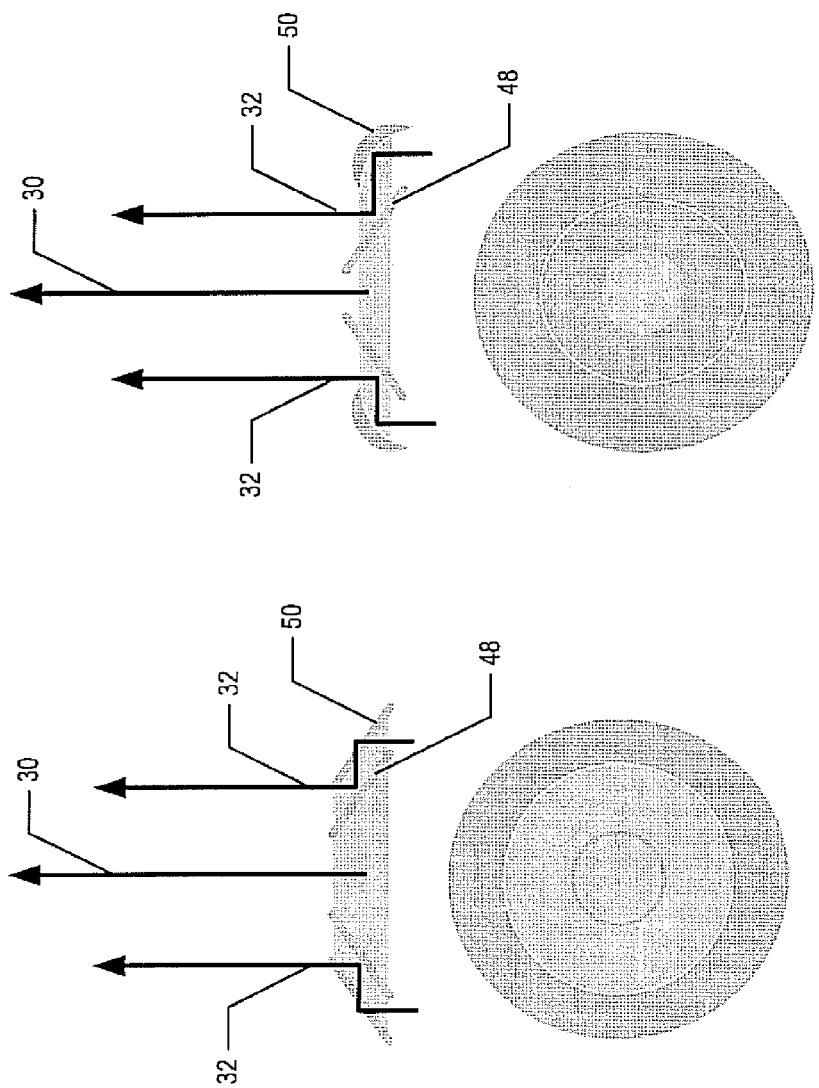

NON-CONTACT TOTAL EMISSION DETECTION METHOD AND SYSTEM FOR MULTI-PHOTON MICROSCOPY

CROSS-REFERENCE TO RELATED APPLICATIONS

This is the national stage of International Application No. PCT/US2010/041723, filed on Jul. 12, 2010, which claims the benefit of U.S. Provisional Patent Application No. 61/224,772, filed on Jul. 10, 2009, the contents of all of which are hereby incorporated herein by reference.

FIELD

This application relates to a microscopes and methods of microscopy, and in particular to multi-photon microscopes and multi-photon methods of microscopy.

BACKGROUND

Laser fluorescence confocal microscopy is an effective technique for producing three-dimensional images. In particular, multi-photon fluorescence excitation microscopy (MPFM) techniques (e.g., two-photon, three-photon, second harmonic generation, sum frequency generation, etc.) can be used to provide optical sectioning by limiting fluorescence excitation to a point source in the focal plane of the microscope. Two-photon fluorescence microscopy (TPFM) has advantages in that it causes less damage to the biological system above and below the focal plane and that longer excitation wavelengths can be used to excite fluorescence from deeper in a sample (e.g., hundreds of microns).

In MPFM, the excitation is limited to the focal plane due to the level of spatial and temporal crowding of photons into a diffraction-limited spot. This crowding increases the probability of a fluorophore absorbing multiple photons before relaxation to the ground state or it increases the probability of coherent scattering events. In the case of (TPFM) in which two photons are of the same wavelength, the excited state is at twice the energy of the photons used for excitation. Since multi-photon absorption is a lower probability event than single photon absorption, a high intensity illumination source is typically required to excite a sufficient number of molecules to be detected. Once the multi-photon excitation condition is met, emission light propagates in all directions from the excited spot of the sample. Because there is no need for using a pinhole aperture for optical sectioning, the opportunity for collecting all of the light, regardless of the direction of propagation, exists when attempting to optimize light collection. Conventional multi-photon microscopes illuminate and collect light through the same objective lens system or in conjunction with a detector placed in the trans-fluorescence pathway. This leads to detecting only a fraction of the light that is emitted from the sample. More light collection means less excitation power is needed and deeper tissue penetration is possible. A total emission detection system for multi-photon spectroscopy that entirely encloses a sample within the device has been previously disclosed in U.S. application Ser. No. 11/979,600, Publication No. US-2008-0063345-A1, the entire contents of being incorporated herein by reference. However, there remains a need for a multi-photon microscope that can obtain improved light collection emitted from a sample that is too large to be enclosed within the device.

SUMMARY

In an embodiment, a multi-photon microscope may include an illumination source for transmitting an illumination light into a housing. An objective lens arrangement defines an aperture and that is disposed inside the housing with the objective lens arrangement being oriented in an optical pathway of the illumination source to direct the illumination light through the aperture of the objective lens arrangement to a focused illumination region of a sample under observation disposed outside the housing. A light collection system is disposed inside the housing with the light collection system having a reflector defining an aperture and arranged proximate the objective lens arrangement such that the aperture of the objective lens arrangement is oriented towards the aperture of the reflector. A detection system is oriented in an optical pathway of the objective lens arrangement and the light collection system for detection of light emitted by the sample, wherein the objective lens arrangement is configured to direct a first portion of emission light that is emitted from the illumination region of the sample under observation in response to being illuminated by the illumination light to the detection system. In addition, the light collection system is configured to direct a second portion of emission light that is emitted from the illumination region of the sample under observation in response to the illumination light to the detection system.

In another embodiment, a method of forming a magnified image may include:
  providing a multi-photon microscope having an illumination source that emits an illumination light through an objective lens arrangement encased inside a housing, the objective lens arrangement comprising at least one objective lens defining an aperture arranged to direct the illumination light for illuminating a sample disposed outside the housing;
  illuminating a portion of the sample through the aperture with the illumination light along an illumination region to cause multi-photon excitations such that an emission light is emitted by the sample;
  redirecting the emission light caused by the multi-photon excitations to a light collection system and the objective lens arrangement for directing the emission light to a detection system; and
  detecting the emission light subsequent to redirecting the emission light, wherein the emission light comprises a first portion of emission light that is redirected by the objective lens arrangement and a second portion of emission light that is redirected by the light collection system.

Another embodiment of the method may further include:
  moving either the sample or the illumination light relative to one another;
  repeating the steps of illuminating a portion of the sample, redirecting the emission light and detecting the emission light subsequent to redirecting the emission light; and/or
  compiling data generated by the detection of the emission light.

Additional objectives, advantages and novel features will be set forth in the description which follows or will become apparent to those skilled in the art upon examination of the drawings and detailed description that follows.

BRIEF DESCRIPTION OF THE DRAWINGS

FIGS. 6A and 6B are simplified illustrations showing two different embodiments of a reflector arrangement for reducing the radial separation between the first portion of emission light that exits the objective lens arrangement and the second portion of emission light directed by the light collection system shown in FIG. 5;

Corresponding reference characteristics indicate corresponding elements among the view of the drawings. The headings used in the figures should be interpreted to limit the scope of the claims.

DETAILED DESCRIPTION

Figure 1:
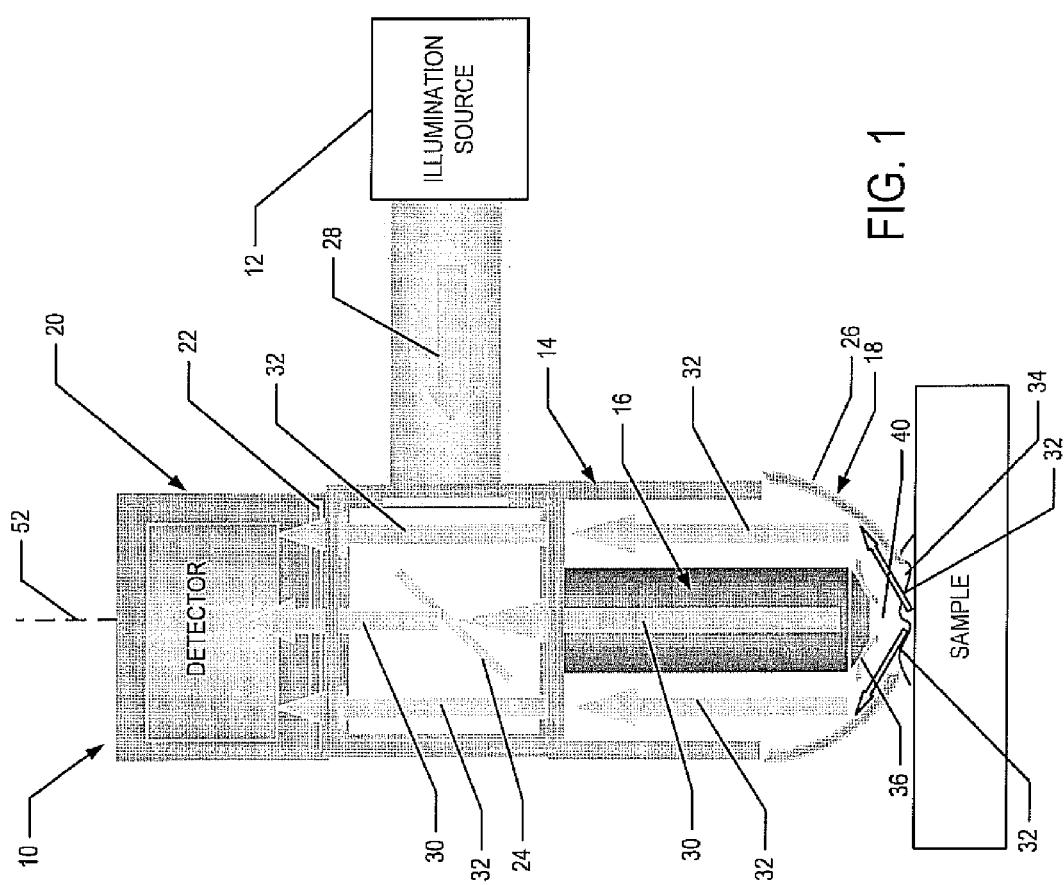
FIG. 1 is a simplified illustration showing an embodiment of a multi-photon microscope.

Multi-photon fluorescence microscopes are specialized optical microscopes having an illumination source for transmitting a light to excite fluorophores within a biological sample being observed by limiting fluorescence excitation to a point source along the focal plane of an objective lens of the multi-photon microscope. Conventional multi-photon microscopes illuminate and collect light through the same objective lens or in conjunction with a detector placed in the trans-fluorescence pathway of the excited sample. Such arrangements lead to detecting only a fraction of the light that is emitted from the sample during excitation, which is inefficient and undesirable.

A multi-photon microscope with a "total emission detection" adaptation that totally encloses a sample within the device itself addresses some of these issues by providing a reflective surface and objective lens arrangement in which the sample is suitable for being encased inside light collection system in order to capture more of the emission light emitted from the sample upon excitation. However, a sample that is too large to be enclosed inside such a device must necessarily be studied outside the device.

As such, embodiments of the multi-photon microscope as set forth herein include particular components, properties and characteristics that address issues related to capturing substantially all of the emission light leaving a sample that is too large to be enclosed inside the device. The multi-photon microscope as described herein uses a light collection system configured to capture substantially all of the "epi" light emitted on, around and above the illumination region of the sample during excitation that is not captured through the aperture of the objective lens when the sample is disposed outside the light collection system of the multi-photon microscope. Further details and embodiments of the multi-photon microscope are discussed in greater detail below.

Referring to the drawings, various embodiments of the multi-photon microscope are illustrated and generally indicated as 10 in FIGS. 1-6. In one embodiment shown in FIG. 1, the multi-photon microscope 10 includes an illumination source 12 that transmits an illumination light 28 for illuminating an illumination region 38 of a sample under observation that is located outside the microscope 10. As used herein, the term "light" is intended to have its broadest meaning and is not intended to be limited to only visible light, and may include, without limitation, infrared, ultraviolet light, and visible light. In one embodiment, the illumination source 12 may be a laser having a power and wavelength selected according to the particular application. In addition, the illumination source 12 may include filters, beam shapers, homogenizers and/or other optical components to collimate, focus and/or redirect the illumination light 28 as desired.

In one embodiment, the illumination light 28 transmitted by the illumination source 12 is reflected by a dichroic mirror 24 that directs the illumination light 28 through a lens system that includes an objective lens arrangement 16 which illuminates the sample along the illumination region 38 by the illumination source 12. A housing 14 encloses the objective lens arrangement 16 including a reflector 26 defining an aperture 34 that encases the distal portion of the objective lens arrangement 16. The reflector 26 may be parabolic and provides a light collection system 18 that collects emission light emitted by the sample during excitation that is not captured by the objective lens arrangement 16 as shall be discussed in greater detail below. The microscope 10 may be moved along the vertical axis to adjust the focus position of the reflector 26. In one embodiment, the reflector 26 has a parabolic configuration, although in other embodiments the reflector 26 may be a toric mirror, elliptical mirror, or a conic mirror. In an embodiment, the reflector 26 may cooperate with other reflecting surfaces. In addition, the reflector 26 may include a high-reflection coating to enhance reflection of the emission light from the sample.

Figure 2:
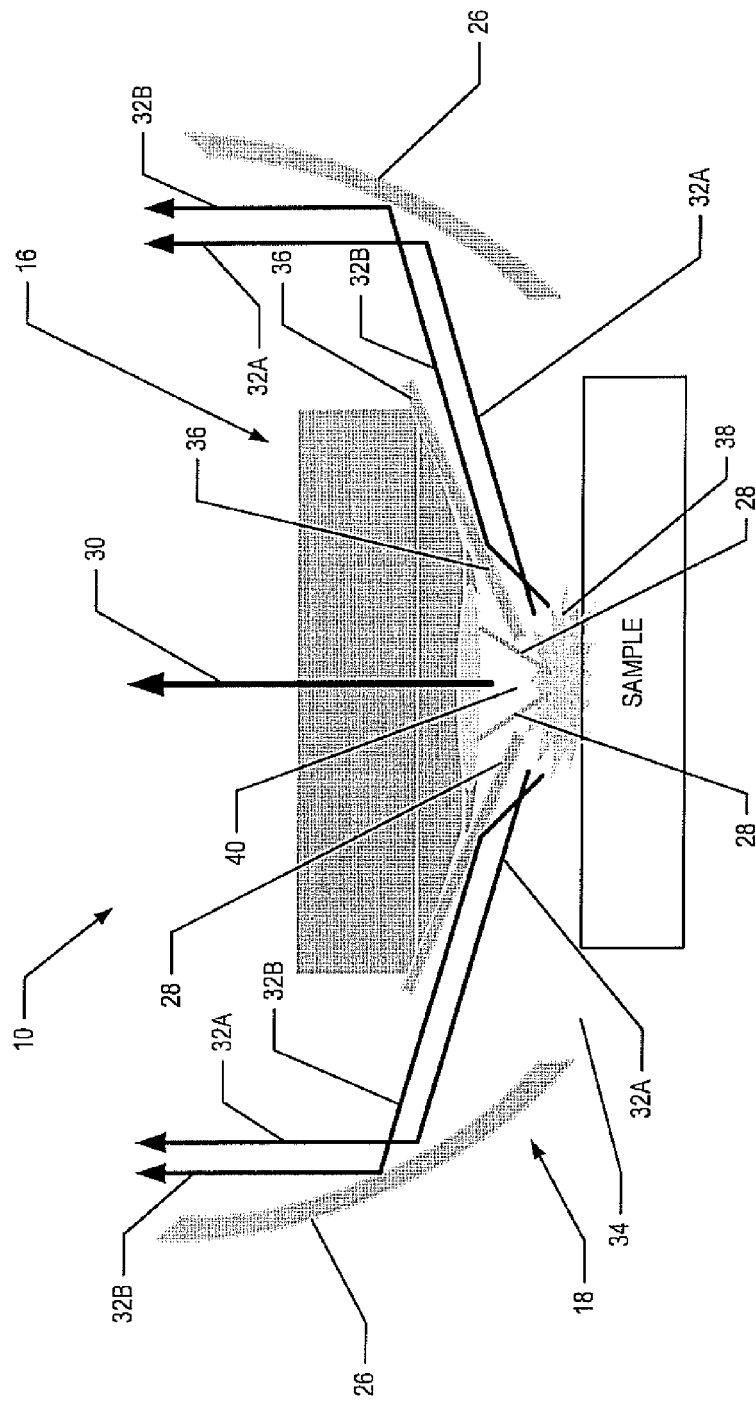
FIG. 2 is an enlarged view of FIG. 1 showing an objective lens arrangement as well as a light collection system of the multi-photon microscope.

Referring to FIGS. 1 and 2, the distal portion of the objective lens arrangement 16 includes an aperture 40 configured to permit the illumination light 28 to illuminate the sample along the illumination region 38 of the sample under observation. The objective lens arrangement 16 is oriented along an optical axis 52 for focusing the illumination light 28 on the illumination region 38 of the sample. In particular, the objective lens arrangement 16 is oriented such that the aperture 40 of the objective lens arrangement 16 is oriented towards and faces the aperture 34 of the reflector 26. In one embodiment, the objective lens arrangement 16 may include a chamfered reflective surface 36 adapted to reflect light emitted from the sample as shall be discussed in greater detail below.

In one embodiment, the objective lens arrangement 16 may include a single objective lens, a plurality of objective lenses and/or include other reflective components. As used herein, the term "lens" shall include refractive, diffractive and gradient refractive index lenses. In an embodiment, the objective lens arrangement 16 can also be an immersion objective lens in which liquid having a refractive index greater than air is provided between the front lens surface and a surface of the sample under observation. Such an immersion objective lens permits a larger numerical aperture, and thus an increase in light acceptance angles when detecting light emitted by the sample during excitation.

After the sample is illuminated by the objective lens arrangement 16, emission light is given off by the sample, which is now in an excited state, as the sample generates a fluorescence signal in response to being illuminated by the illumination source 12. For example, the emission light can be fluorescent light emitted from the sample from the excited states that are reached due to multi-photon absorption by the sample.

Referring particularly to FIG. 2, a first portion of emission light 30 enters the aperture 40 of the objective lens arrangement 16 and is directed to the detection system 20 located proximal the objective lens arrangement 16, while emission light not captured through the aperture 40, referred to as the second portion of emission light 32, may be reflected off the interior surface of the reflector 26 and directed towards the detection system 20 in a coaxial path relative to the first portion of emission light 30. The reflector 26 and objective lens arrangement 16 are constructed such that the first and second portions of the emission light 30 and 32 constitute substantially all of the emission light being emitted by the sample on and above the illumination region 38. As used herein, "on, around and above" refers to the plurality of emission angles, which leave the sample from horizontal to vertical if the sample is flat, or from vertical t slightly below horizontal if the sample has a convex configuration. As noted above, the reflector 26 may include a high-reflection coating to enhance the reflection of the second portion of emission light 32.

The detection system 20 is adapted to detect the first portion of emission light 30 and the second portion of emission light 32, which may have a different spectral distribution than the spectral distribution of the illumination light 28. In one embodiment, a photomultiplier (not shown) may be used with a detection system 20. In another embodiment, the detection system 20 may include a filter arrangement 22, which can be a hi-pass filter, band-pass filter, low-pass filter and/or neutral density filters. In an embodiment, avalanche photodiodes (not shown) may also be used with the detection system 20 for detecting first portion of emission light 30 and second portion of emission light 32. The dichroic mirror 24, which reflects the illumination light 28 through the objective lens arrangement 16, also allows the first portion of emission light 30 to pass through the mirror 24 with little attenuation. In one embodiment, the objective lens arrangement 16 may include additional optical components for image formation and magnification.

In operation, a sample under observation located either substantially inside or outside, but proximate, to aperture 34 of the reflector 26 may be illuminated by illumination light 28 to produce an excited state within the sample such that first and second portions of emission light 30 and 32 are emitted by the sample on, around and above the illumination region 38. As illustrated in FIG. 2, the second portion of emission light, designated 32A, is emitted from illumination region 38 at an exit angle that exceeds the acceptance cone of the objective lens arrangement 16 as well as avoid being reflected off the body of objective lens arrangement 16, thereby causing the second portion of emission light 32A to be directly reflected off the parabolic reflector 26. Another second portion of emission light, designated 32B, is emitted from the focal plane 38 at an exit angle that also exceeds the acceptance cone of the objective lens arrangement, but is less than the angle required to avoid the body of the objective lens arrangement 16, thereby causing the second portion of emission light 32B to reflect off the chamfered reflective surface 36 of the objective lens arrangement 16 before being reflected off the inner surface of the reflector 26. As used herein, the term "exit angle" means that angle of the second portion of emission light 32 from the sample relative to the optical axis 52 of the objective lens arrangement 16. As further used herein, the term "acceptance cone" means a range of angles that emission light being emitted by the sample must fall within in order to be directed or not directed through the aperture 40 of the objective lens arrangement 16 and further determines whether such emitted light is first portion of emission light 30 (e.g., emission light that travels through the aperture 40) or second portion of emission light 32 (e.g., emission light that does not travel through the aperture 40 and is redirected by the reflector 26).

During this operation, the first portion of emission light 30 is emitted from the sample at an angle that does not exceed the acceptance cone of the objective lens arrangement 16, and therefore the first portion of emission light 30 enters the aperture 40 of the objective lens arrangement 16 and is directed to the detection system 20 along a pathway that is coaxial and proximate to the pathway taken by the second portion of emission light 32. In an embodiment, the detection system 20 detects both the first portion of emission light 30 directed by the objective lens arrangement 16 and the second portion of emission light 32 directed by the reflector 26, thereby providing substantially more light to the detection system 20 than if the first portion of emission light 30 from the objective lens arrangement 16 was alone collected by the detection system 20. For example, the multi-photon microscope 10 has detected in a range of between 2-3 times additional emission light from a biological sample, such as a mouse.

Figure 3:
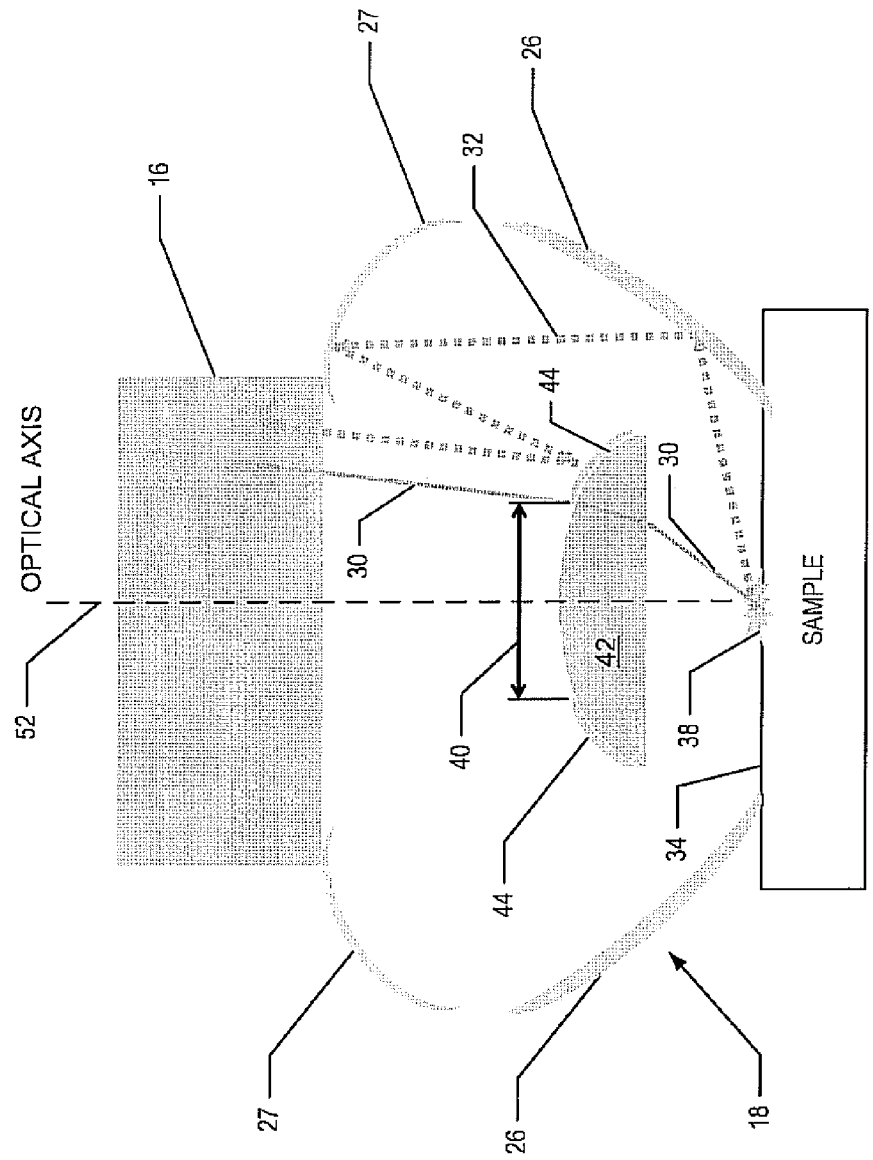
FIG. 3 is a simplified illustration showing one embodiment of a structural arrangement for directing a second portion of emission light into a coaxial path that is closely aligned to a first portion of emission light emitted by a sample.

Referring to FIG. 3, a simplified illustration of one embodiment of the light collection system 18 and objective lens arrangement 16 is shown. In one embodiment, the objective lens arrangement 16, exclusive of the central objective lens 42, provides a means for directing the second portion of emission light 32 into a coaxial pathway that is closely aligned with and proximate to the first portion of emission light 30. The objective lens arrangement 16 includes a central objective lens 42, which defines an aperture 40 and further includes a peripheral mirrored surface 44. As noted above, the first portion of emission light 30 captured through the aperture 40 is directed through the central objective lens 42. The acceptance cone of aperture 40 is unobstructed by the peripheral mirrored surface 44. In this embodiment, the central objective lens 42 may include the chamfered reflective surface 36, which is not illustrated to simplify FIG. 3.

In an alternative embodiment, the second portion of emission light 32 may be directly reflected off the reflector 26 and then reflected off a secondary reflector 27, such as a concave reflector which directs the second portion of emission light 32 to the peripheral mirror surface 44, such as a convex reflector, of the central objective lens 42. The second portion of emission light 32 is then reflected off the peripheral mirror surface 44 along a pathway that is coaxial and proximate to the pathway of the first portion of emission light 30 for detection by the detection system 20. This arrangement of a concave reflector and a convex reflector acts collectively as a compound Cassegrain reflector, except the aperture 40 is unobscured and the acceptance angles for the second portion of emission light 32 exceed those acceptance angles of conventional Cassegrain objective lenses.

Figure 4:
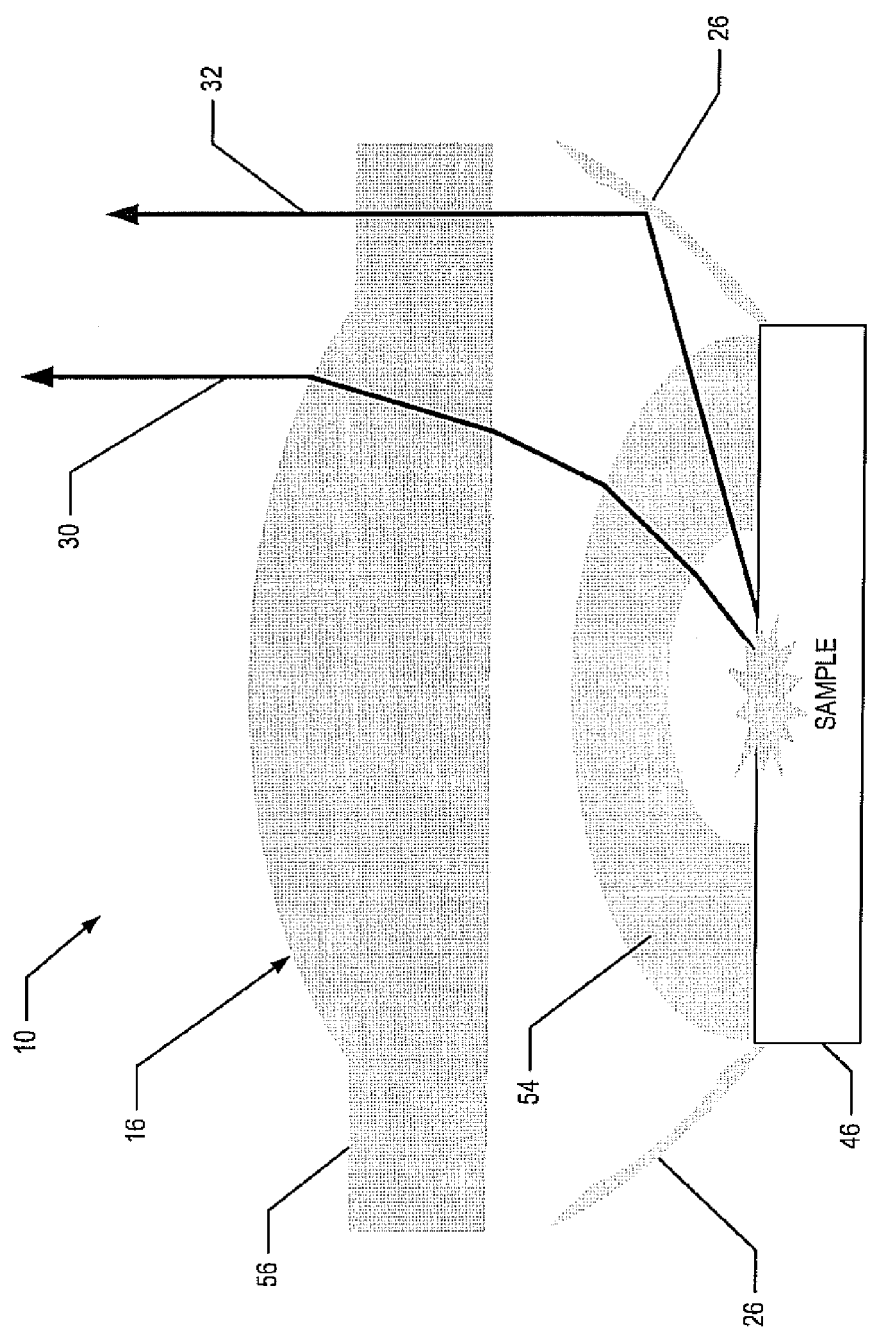
FIG. 4 is a simplified illustration showing another embodiment of a structural arrangement for directing the second portion of emission light into a coaxial, proximate pathway relative to the first portion of emission light.

Referring to FIG. 4, a simplified illustration of another embodiment is shown for directing the second portion of emission light 32 along a pathway that is coaxial and proximate to the pathway of the first portion of emission light 30. In this embodiment, a concave lens 56 similar to a conventional high numerical aperture water objective lens is oriented toward the sample and surrounded by the parabolic reflector 26 such that the second portion of emission light 32 is reflected off the parabolic reflector 26 and is then transmitted through a collimation lens 56 along a pathway that is coaxial and proximate to the first portion of emission light 30 that exits the collimation lens 56 along a similar pathway. In this embodiment, the collimation lens 56 may have a compound curvature intended to act as a normal objective collimation lens for smaller exit angles, but with a reduced optical power at its periphery to direct the second portion of the emission light 32 into the detection system 20 similar to the first portion of emission light 30.

Figure 5:
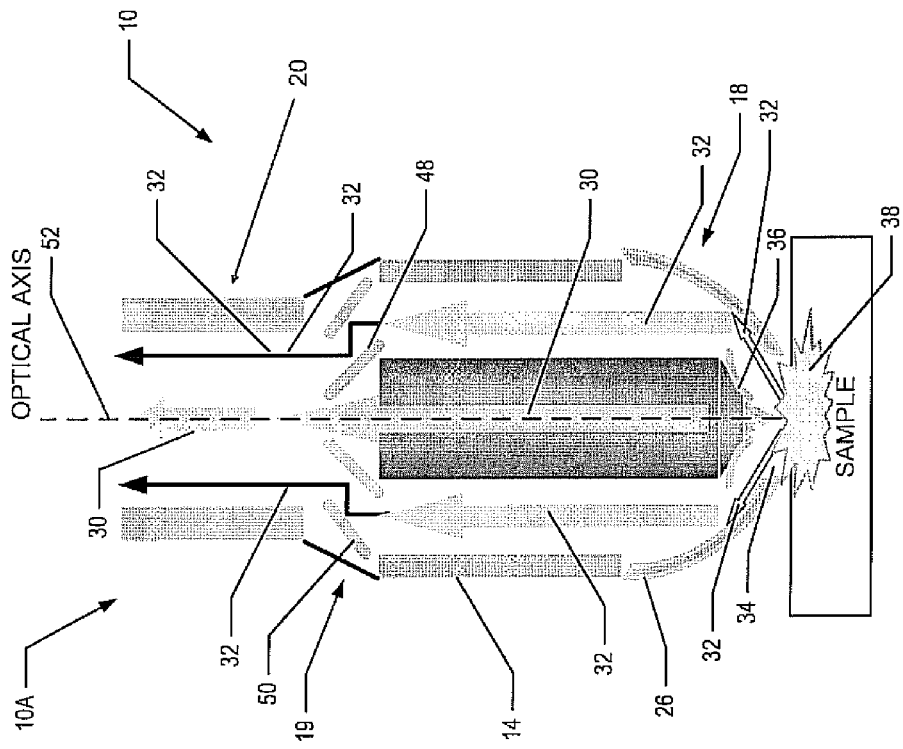
FIG. 5 is a simplified illustration of another embodiment of the multi-photon microscope.

Referring to FIGS. 5 and 6A, an embodiment of the multi-photon microscope, designated 10A, is shown which is similar to the other embodiment of multi-photon microscope 10 with the exception that this embodiment includes a means for reducing radial separation between the first portion of emission light 30 that exits the objective lens arrangement 16 and the second portion of emission light 32 that is directed toward the detection system 20. In the multi-photon microscope 10, the first portion of the emission light 30 travels as a solid cylinder toward detection by the detection system 20 and the second portion of emission light 32 forms a hollow, coaxial cylinder of emission light traveling in the same direction parallel to the optical axis 52. The separation between the first portion of emission light 30 and the second portion of emission light 32 is determined by the size and focal length of the reflector 26. Many microscopes have detection apertures commensurate with the size of the objective lens arrangement 16. As such, it is advantageous to reduce the radius of the second portion of emission light 32 defined by the hollow cylinder of emission light and pass the second portion of emission light 32 with the first portion of emission light 30 into such a reduced aperture of the detection system 20. The multi-photon microscope 10A has a reflector arrangement 19 that includes an inner reflector 48 defining a central aperture disposed inside an outer reflector 50 that collectively defines a concentric opening with the inner reflector 48.

As shown, the first portion of emission light 30 passes undisturbed through the central aperture of the inner reflector 48, while the second portion of emission light 32 is reflected by the inner surface of the outer reflector 50 radially inward to the outer surface of the inner reflector 48 which then directs the second portion of emission light 32 in an axial direction parallel to the optical axis 52. As such, the second portion of emission light 32 exits the reflector arrangement 19 along a pathway that is substantially parallel and more proximate to the pathway taken by the first portion of emission light 30.

Referring to FIG. 6B, the inner and outer reflectors 48 and 50 may have a curved configuration in order to add or subtract optical power and facilitate co-propagation of the first and second portions of the emission light 30 and 32 to the detection system 20. In some embodiment, the cone angles of the inner and outer reflectors 48 and 50 may be other than 45 degrees, although a range between 10-80 degrees is contemplated.

It should be understood from the foregoing that, while particular embodiments have been illustrated and described, various modifications can be made thereto without departing from the spirit and scope of the invention as will be apparent to those skilled in the art. Such changes and modifications are within the scope and teachings of this invention as defined in the claims appended hereto.

What is claimed is:

1. A multi-photon microscope comprising: an illumination source for transmitting an illumination light into a housing; an objective lens arrangement defining an aperture and disposed inside the housing, the objective lens arrangement being oriented in an optical pathway of the illumination source to direct the illumination light through the aperture of the objective lens arrangement to a focused illumination region of a sample under observation disposed outside the housing; a light collection system disposed inside housing, the light collection system having a reflector defining an aperture and arranged proximate the objective lens arrangement such that the aperture of the objective lens arrangement is oriented towards the aperture of the reflector; and a detection system oriented in an optical pathway of the objective lens arrangement and the light collection system for detection of light emitted by the sample; wherein the objective lens arrangement is configured to direct a first portion of emission light that is emitted from the illumination region of the sample under observation in response to being illuminated by the illumination light to the detection system; wherein the light collection system is configured to direct a second portion of emission light that is emitted from the illumination region of the sample under observation in response to the illumination light to the detection system; and wherein the objective lens arrangement and the light collection system are configured such that the first and second portions of emission light captured by the detection system collectively constitute emission light on, sideways or above the illumination region.

2. The multi-photon microscope of claim 1, wherein the illumination region is the illumination region of the objective lens arrangement that intersects the biological sample under observation.

3. The multi-photon microscope of claim 1, wherein the first and second portions of emission light have a different spectral distribution than a spectral distribution of the illumination light.

4. The multi-photon microscope of claim 1, wherein the objective lens arrangement includes a chamfered reflective surface defined proximate the aperture of the objective lens arrangement.

5. The multi-photon microscope of claim 4, wherein the chamfered reflective surface reflects a portion of the second portion of emission light such that the second portion of emission light follows a pathway that is coaxial relative to the first portion of emission light.

6. The multi-photon microscope of claim 1, wherein the illumination source comprises a laser to provide laser light.

7. The multi-photon microscope of claim 1, wherein the first portion of emission light and the second portion of emission light have a coaxial relationship when detected by the detection system.

8. The multi-photon microscope of claim 1, wherein the reflector is a parabolic reflector.

9. The multi-photon microscope of claim 1, wherein the reflector is a toric mirror.

10. The multi-photon microscope of claim 1, wherein the reflector is a conic mirror.

11. The multi-photon microscope of claim 1, wherein the reflector is an elliptical mirror.

12. The multi-photon microscope of claim 1, wherein the reflector comprises a high-reflection coating to enhance the reflection of the second portion of emission light.

13. The multi-photon microscope of claim 1, wherein the light collection system comprises an unobscured Cassegrain reflector ring arranged to direct at least a portion of the second portion of emission light from the reflector to the detection system, the Cassegrain reflector comprising a concave reflector and a hollow convex reflector.

14. The multi-photon microscope of claim 13, wherein the inner reflector defines a central aperture that permits the first portion of emission light to pass therethrough without interference.

15. The multi-photon microscope of claim 1, further comprising a coaxial conic reflector arrangement comprising an inner reflector disposed within an outer reflector arranged to reflect the second portion of emission light to the detection system in coaxial relationship with the first portion of emission light.

16. A method of forming a magnified image comprising:
providing the multi-photon microscope of claim 1;
illuminating a portion of the sample through the aperture with the illumination light along the illumination region to cause multi-photon excitations such that an emission light is emitted by the sample;

redirecting the emission light caused by the multi-photon excitations to the light collection system and the objective lens arrangement for directing the emission light to the detection system; and detecting the emission light subsequent to redirecting the emission light.

17. The method for forming a magnified image according to claim 16, further comprising moving either the sample or the illumination light relative to one another.

18. The method for forming a magnified image according to claim 17, further comprising repeating the steps of illuminating a portion of the sample, redirecting the emission light and detecting the emission light subsequent to redirecting the emission light.

19. The method for forming a magnified image according to claim 18, further comprising compiling data generated by the detection of the emission light.

* * * * *